United States Patent [19]

Jonas

[11] Patent Number: 5,134,380
[45] Date of Patent: Jul. 28, 1992

[54] ICING DETECTOR AND METHOD

[76] Inventor: Otakar Jonas, 1113 Faun Rd., Wilmington, Del. 19803

[21] Appl. No.: 588,488

[22] Filed: Sep. 26, 1990

Related U.S. Application Data

[63] Continuation of Ser. No. 827,630, Feb. 10, 1986, abandoned.

[51] Int. Cl.⁵ .................. G01R 27/22; G01R 27/26
[52] U.S. Cl. .................... 324/674; 324/663; 324/693; 340/602; 340/580
[58] Field of Search ............. 324/663, 664, 670, 671, 324/674, 689, 694, 685, 724, 693; 340/602, 580, 962

[56] References Cited

U.S. PATENT DOCUMENTS

| | | | |
|---|---|---|---|
| 3,882,381 | 5/1975 | Gregory | 340/602 X |
| 4,135,151 | 1/1979 | Rogers et al. | 324/61 R |
| 4,333,004 | 6/1982 | Forgue et al. | 340/580 X |
| 4,468,610 | 8/1984 | Hanson | 324/61 R |
| 4,522,060 | 6/1985 | Murata et al. | 324/65 R X |
| 4,604,612 | 8/1986 | Watkins et al. | 340/582 |

FOREIGN PATENT DOCUMENTS 0883836 11/1981 U.S.S.R. ........................ 324/61 R

Primary Examiner—Jack B. Harvey

[57] ABSTRACT

A device and method for detecting the nature and condition of ice, water or air on a surface by producing output signals by measurement of dynamic dielectric constant and electrical conductivity of the material on the surface and decoding digital signals therefrom to display information as to the condition. More particularly, a sensing apparatus for producing output voltage signals in response to the formation of ice, water or air at a surface and processing a combination of voltage levels as digital signals to decoding circuitry to provide information which is independent of contamination and impurities and of the size and nature of sensor elements.

8 Claims, 4 Drawing Sheets

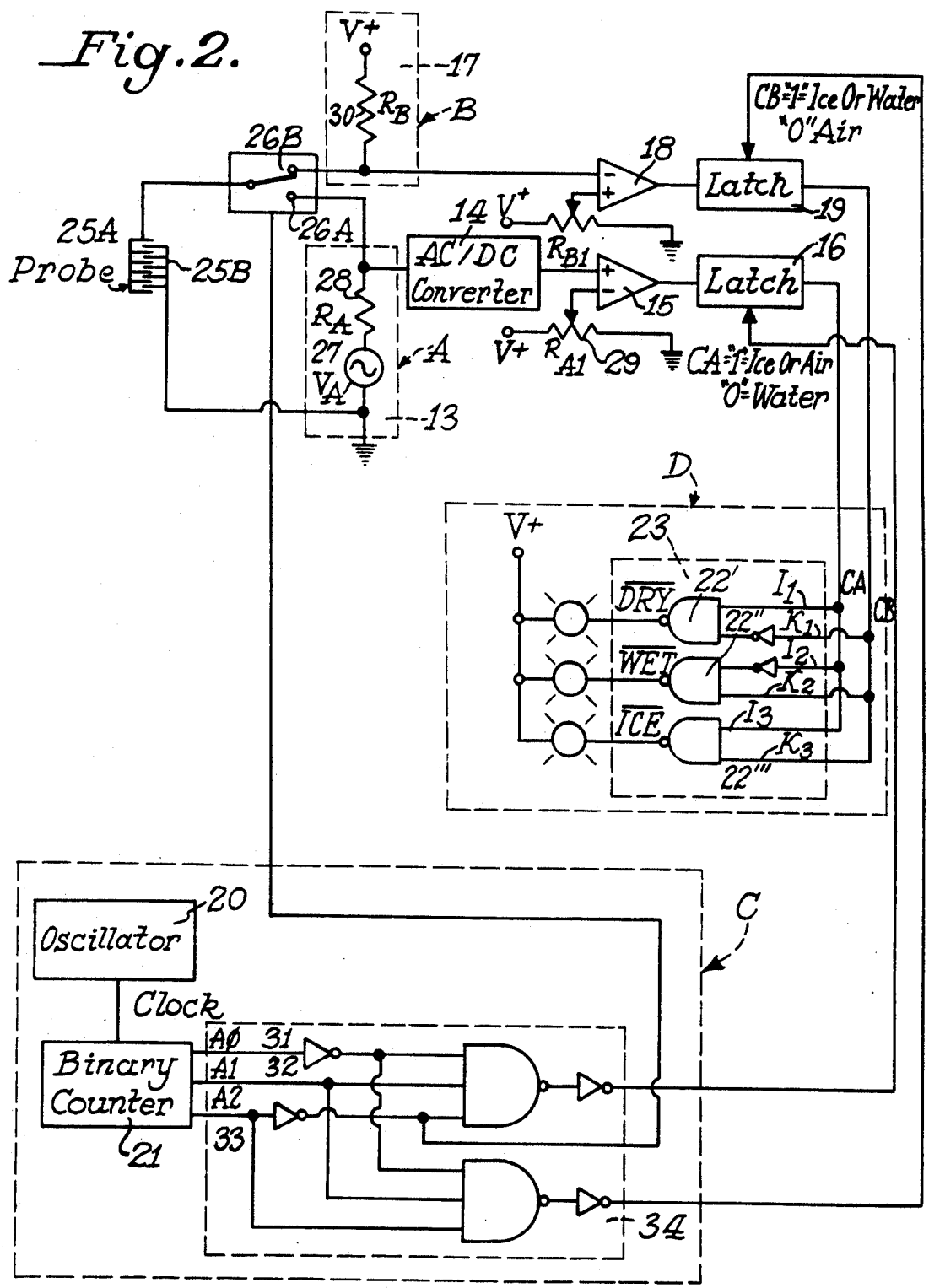

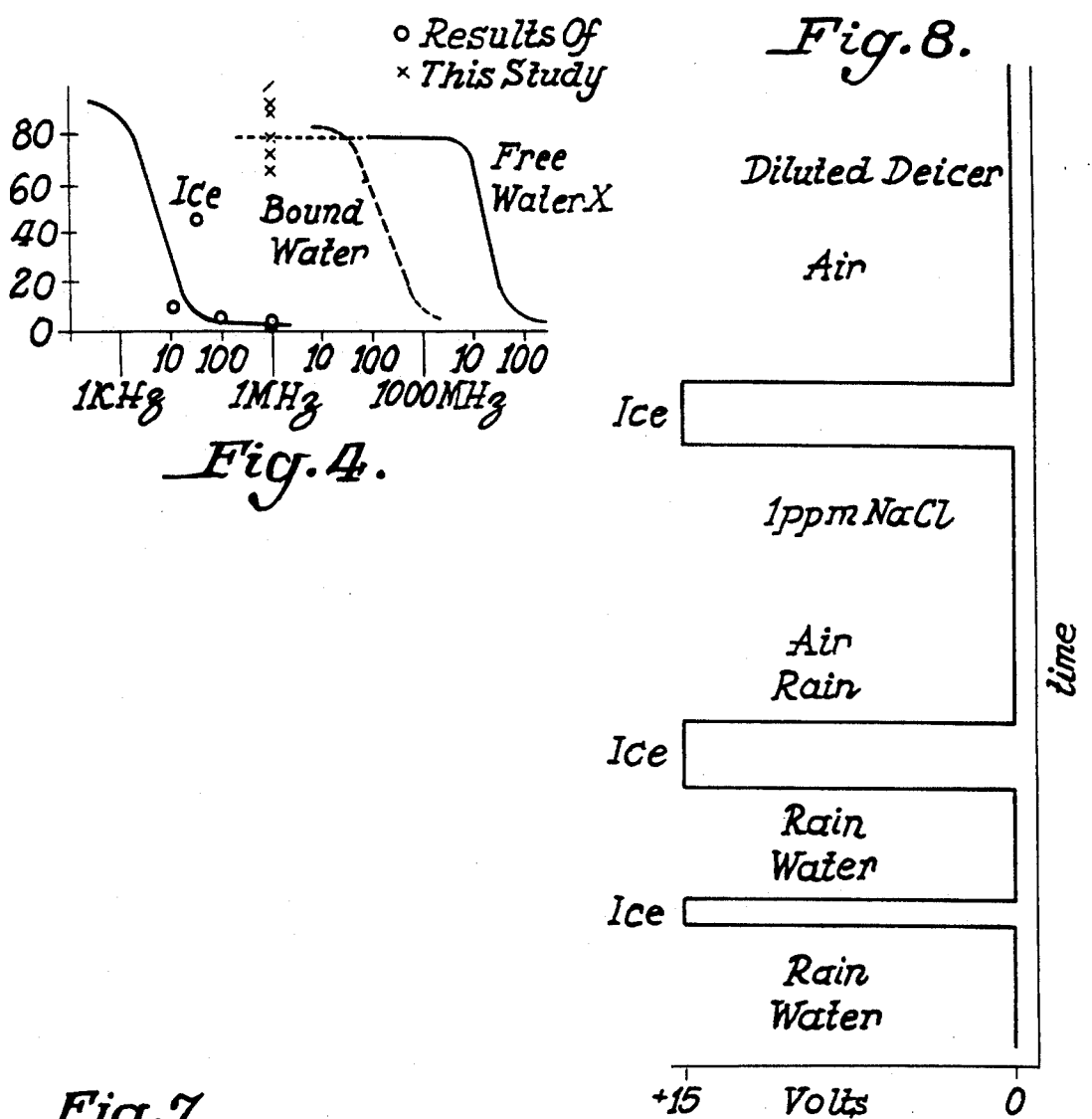
Fig. 8.
Fig. 4.
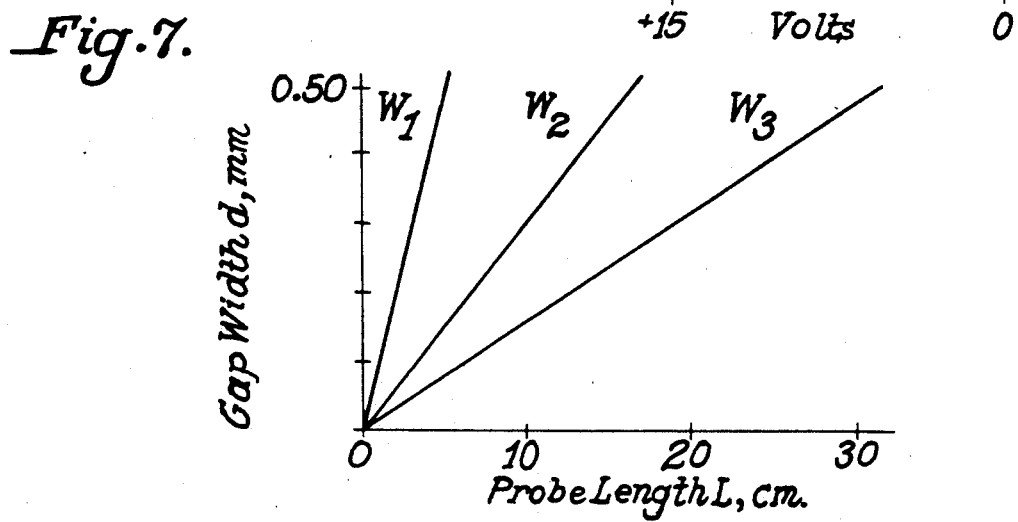
Fig. 7.

ICING DETECTOR AND METHOD

CROSS REFERENCE TO RELATED APPLICATIONS

This application is a filewrapper continuation of U.S. application Ser. No. 827,630 filed Feb. 10, 1986, now abandoned for Icing Detector By Otakar Jonas.

BACKGROUND OF THE INVENTION

This invention relates to a means and method for determining the condition of a surface with respect to ice, dryness, or water present at the surface. More particularly, it relates to systems for detecting icy, wet, and dry conditions on surfaces of aircraft, helicopter rotors, gasoline engine carburetors, roads, bridges, exposed structures, airport runways, taxiways, and refrigerator and freezer surfaces. The system can also be applied to surface condition monitoring of agricultural crops.

The presence, or absence, of ice at certain surfaces may be a fact of critical importance. The monitoring of ice and wetness on roads, bridges, airport surface, aircraft structures, and other surfaces necessarily exposed to atmospheric conditions is desirable.

Capacitance sensors for monitoring icing conditions have been proposed in the U.S. Pat. Nos. 3,428,890, 3,684,953, 3,873,927 and 3,882,381. All the above capacitance systems require bulky sensors which are not applicable for icing measurements under flow conditions, such as needed for aircraft applications. The system described in the U.S. Pat. Nos. 3,873,927, 3,882,381 requires complex interpretation of the measured variables and is, therefore, bulky, and expensive.

Thus it is seen that sensors for monitoring surface areas for testing the conditions of water for detecting icing conditions have been proposed with sensing elements of an undesirable size and shape and which are not amenable to positioning on a surface which is intended to receive currents of air flowing over the surface. These sizeable sensor elements among other undesirable attributes would interfere with the flow of air such as over the surface of an airplane wing or a helicopter rotor.

It will also be noted that other ice detecting systems which provide less obtrusive sensor electrodes employ means for interpreting the conditions and indicating icing which involve complex operations in providing notification of icing conditions. Such complex operations are unduly sensitive in performance and therefore unreliable in a procedure where reliability is of prime importance.

Other means such as mechanical vibration, air flow, and temperature testing sensors are even less reliable and encounter more interference.

Such monitoring systems encounter conditions which can hinder accurate and reliable operation of means for testing and identifying the presence or absence of water or ice.

SUMMARY OF THE INVENTION

It is an object of this invention to provide a device to quickly detect and signal change in state of water and ice at a surface.

It is a further object to provide a testing device for ice and water at a surface in which the test requirement and results do not restrict the size or shape of the probes or the conductive material it is composed of.

Still another object of the present invention is to provide a system for detecting the icing, wetness, or dryness of a surface free of misinformation from ambient conditions and is insensitive to contamination and impurities in the ice or water or air.

This and other objects of the present invention will become more apparent from the following description taken together with the accompanying drawings.

BRIEF DESCRIPTION OF THE DRAWINGS

FIG. 2 is a schematic diagram of a system according to the present invention;

FIG. 4 is a schematic diagram of an electrical circuit for measuring dynamic dielectric constant with a probe according to this invention;

FIG. 7 is a graph showing icing probe scaling relationships according to this invention; and FIG. 8 is a graph showing the output voltages of the circuit of FIGS. 1 and 2.

DESCRIPTION OF THE PREFERRED EMBODIMENT

The present invention utilizes measurements of dyanmic dielectric constant and electrical conductivity with probes at a surface to detect the presence or absence of water or ice and consequently observe and report a phase change, such as water to ice, at the surface.

Figure 1:
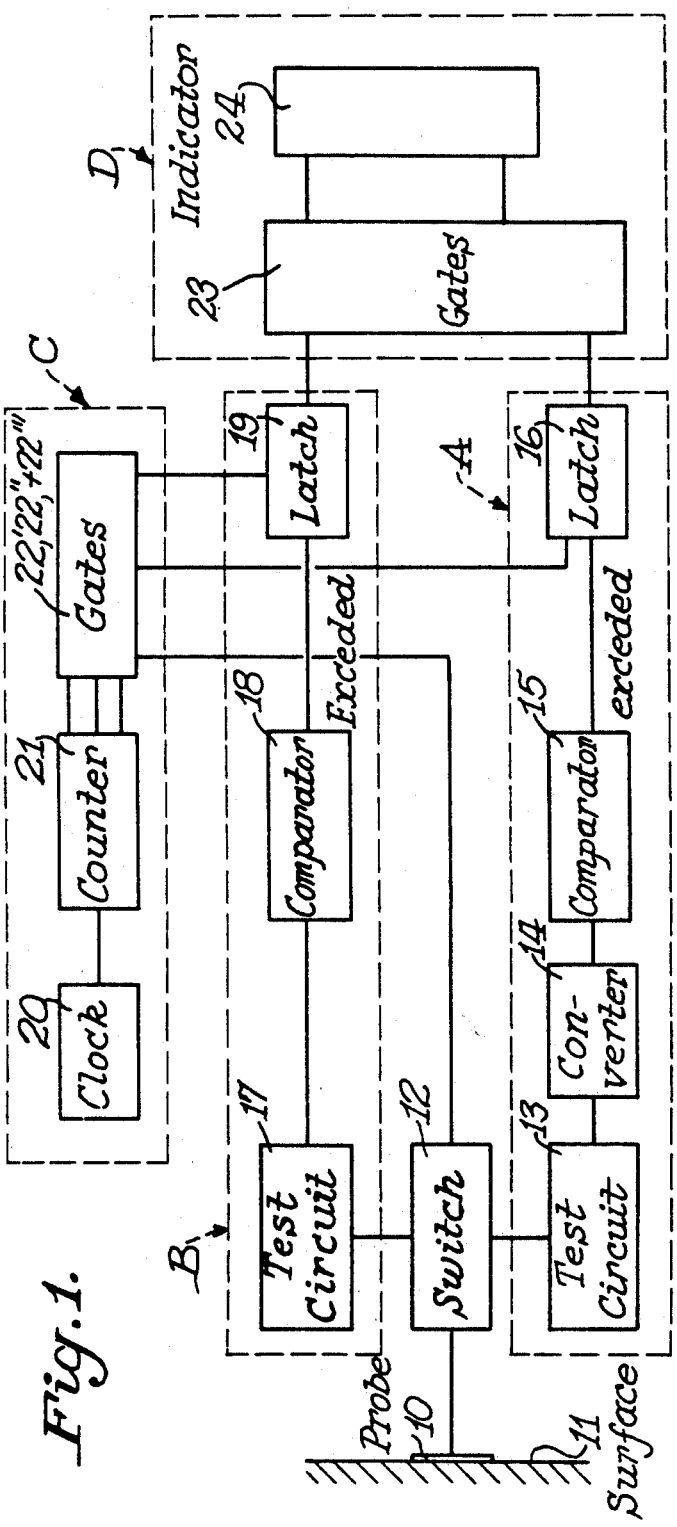
FIG. 1 is a block diagram of the system of this invention.

FIG. 1 shows a system for monitoring a surface condition with a probe for detecting dry, wet, or ice conditions and displaying the detected status with display lights. This system is designed to determine whether the surface at the probe is iced, wet, or dry by alternatively measuring the dynamic dielectric constant and the electrical conductivity of the substance at the probe and note the nature and phase of this substance in terms of voltage output which is employed in a digit comparator to produce the digit 1.

FIG. 1 is a block diagram showing an embodiment of the invention. A probe 10 at a surface 11 is connected to a single-pole double-throw switch 12 which alternatively connects the probe 10 to a dielectric measurement circuit A, or a conductivity measurement circuit B.

In FIG. 1, the probe 10 is in contact with the icing conditions existing at surface 11, for example an airplane wing surface. The surface 1 can be an integral part of the probe structure. The substance or substances at and on the surface and providing this surface conditions, being in contact with the probe, forms a part of the electrical circuits to which the probe is connected through the switch 12. The probe 10 is connectible, through switch 12 to the dielectric constant measuring circuit A or the electrical conductivity measuring circuit B. With the probe 10 switched into connection in circuit A, an output voltage is produced in the dielectric test circuit means 13 which is a product of the function of the test means 13 with the probe 10 and the dielectric constant of the substance in contact with probe 10 at the surface 11. The dynamic dielectric constant of water at AC frequencies near 1 MHz is at least twice that of ice, thus reflecting the difference between ice and water. This output voltage is converted to DC in the converter 14 which is transmitted to a comparator 15 where it is compared with a reference voltage from a standard variable resistance 29 as shown in FIG. 2. If the output voltage is less than the reference voltage, the comparator 15 produces a positive pulse or "1" when the test measurement from test means 13 becomes stable. If the reference voltage is less, then the comparator 15 produces a negative pulse digital or "0" as the output voltage is grounded out. The positive pulse or digital "1" or the absence of the pulse or digital "0" which is the output of the comparator 15 is latched in a latch 16. The latch 6 is a circuit for storing the information as to the surface condition, and is bistable having 2 digital outputs, referred to as digital 1 for a logic 1 level and digital 0 for a logic 0 level. As explained in greater detail in relation to FIG. 2 when the switch 12 connects the probe 10 to the dielectric test means 13, the AC voltage output from the test means 13 is substantially higher for ice than for water. Consequently, the output of the comparator 15 to the latch 6 is a digital output signal "1" for ice and air and digital signal output "0" for water.

With the probe 10 switched into connection with circuit B, the electrical conductivity of the substance at probe 10 at surface 11 is tested and output voltage is produced in conductivity test circuit means 17, which is a product of the function of the test means 17 with the probe 10 and the electrical conductivity of the substance in contact with the probe 10 at the surface 11.

The resistance at the probe 10 is substantially greater for air at the surface 11 than the probe 10 resistance for ice and/or water. The conductivity circuit produces an output voltage directly relating to the difference in conductivity between ice and/or water on the one hand and air on the other. This output voltage is transmitted to a comparator 18 where it is compared with a reference voltage and produces a positive pulse or "1" if the probe resistance in the circuit B is less than 20M ohms which is the resistance range of the probe resistance with water or ice at the probe 10 and surface 11. The output of comparator 18 is latched in a latch 19. Conversely, the absence of ice or water at surface 11 provides a probe resistance with air which is above 20M ohms. This probe resistance above 20M ohms in circuit B switches the latch 19 to a "0". As explained in greater detail in relation to FIG. 2, when switch 12 connected the probe 10 to the conductivity test means 17, the DC voltage at the probe is the product of V times probe resistance divided by a series resistance plus the probe resistance. Stated as, $$DC\ voltage = \frac{V^+ \times Rprobe}{R_B + Rprobe}$$

The output of the comparator 18 to the latch 19 is a "1" for ice or water and a "0" for air.

A sequencing circuit C commands the connections of circuits A and B with the probe 10 and the reception and storing in the latches 16 and 19 of the output data generated in each circuit A and B. The circuit C is comprised of a clock 20, a counter 21, and a gate network having gates 22', 22" and 22'''. A sequence of clock intervals provided by the clock 20 to the counter 21 defines the time periods during which the respective circuits A and B are selected for connection to the probe 10. Further, during the period of connection of the circuits A or B, the gates 22', 22", and 22''' latch the respective latch 16 or 19 to the circuit output, at which interval the digital output "1" or "0" is accordingly latched for decoding stage 23 and the results of the testing of the surface 11 are shown by the display indicators 24.

FIG. 2 is a more detailed diagram of an embodiment of the apparatus illustrated in FIG. 1. In FIG. 2, the probe electrodes 25B are connected to ground while electrodes 25A are connected to the single pole double throw switch with contacts 26A and 26B arranged so that the electrodes 25A may be connected selectively to either pole contact 26A or contact 26B. The switch 12 connects the probe 10 either to the dielectric measurement circuit "A", or the conductivity measurement circuit "B". When the switch is in position A, a 1 MHz, 3 volt peak amplitude sinewave oscillator 27 is connected in series with a resistance 28 and the probe 10. The AC voltage at the top of resistance 28 equals VA*Zprobe/(RA+Zprobe) where VA=peak voltage, RA=resistance in ohms of resistance 28, Zprobe=impedance at probe 10 in ohms. For ice, this voltage approaches peak voltage, and for water it approaches zero volts. The peak AC voltage is converted to DC and compared to the wiper voltage of the potentiometer 29, set to roughly VA/2. Consequently, the output of comparator 15 is "1" for ice or air and "0" for water. After the circuit has become stable, the output of the comparator is latched and remains constant until the next time it is latched.

When the switch is in position "B", a positive voltage V+ is connected in series with resistance 30 and the probe 10. The DC voltage at the top of the probe 10 equals V+*Rprobe/(R_B+Rprobe). $R_B$ of resistance 30 is typically 2M ohms, and with the wiper voltage of potentiometer $R_{B1}$ set to 0.9×V+, the comparator 18 output will be logic "1" for probe resistance below 20M ohms (ice or water), and logic "0" for resistance 20M ohms and greater (air). Similarly to circuit A, the B output is latched when the measurement is stable.

The digital outputs stored in the latches 16 and 19 provide the data which is decoded by the display logic circuitry D to record the condition identified by the testing at the probe 10. The display logic circuit D includes the three gates 22', 22", and 22''', each connected to both of the latches 16 and 19. The digital information stored in the latches 16 and 19 is written out from the latches 16 and 19 to the gates 22', 22", and 22''' at timed intervals synchronized by the sequencing circuit C. The latched information from the latches 16 and 19 is decoded in the gates to result in identification of the conditions sensed by the testing at the probe 10 as follows:

Where OA represents the digital output information in latch 16 from the dielectric constant measuring circuit A and OB represents the digital output information from the conductivity measuring circuit B, "1" represents a digital 1 and "φ" represents a digital φ and DRY represents the absence of water, WET represents liquid water, and ICE represents frozen water. The logic of the display logic circuit D decodes the data to identify the sensed condition.

| Condition | When |
|---|---|
| DRY | $O_B$ = "0" and $O_A$ = "1" |
| WET | $O_B$ = "1" and $O_A$ = "0" |

| Condition | When |
|---|---|
| ICE | $O_B$ = "1" and $O_A$ = "1" |

The logic circuitry D is comprised of gates 22', 22", and 22''' in the gate network. This logic circuitry decodes the digital information stored in the latches 16 and 19 to convert the binary coded input signal received from latches 16 and 19 to identify the conditions at the surface. The latch 6 generates digital signals on the output lines $I_1$, $I_2$ and $I_3$ to the gates 22', 22" and 22''' respectively. The latch 19 generates digital signals on output lines $K_1$, $K_2$ and $K_3$ to gates 22', 22", and 22''' respectively. The data state of the latches 16 and 19 is read for determination as either a logic 1 or logic 0 level. Writing out the data states of the latches 16 and 19 to the decoding stage 23 and the gates 22', 22", and 22''' indicates the surface conditions which are decoded to desirable information.

When the digital signals from the latches 16 and 19 on the output lines $I_1$, $I_2$ and $I_3$, $K_1$, $K_2$ and $K_3$ the gates 22', 22", and 22''' are actuated as follows.

The gate 22' when the digital signal of $I_1$ is logic 1 level and the digital signal of $K_1$ is logic 0 level then the surface condition is Dry. The gate 22' when the digital signal on $I_2$ is 0 level and the digital signal on $K_2$ is 1 level, then the surface condition is Water. The gate 22''' when the digital signal is $I_3$ is 1 level and the digital signal $K_3$ is 1 level then the surface condition is Ice.

Figure 3:
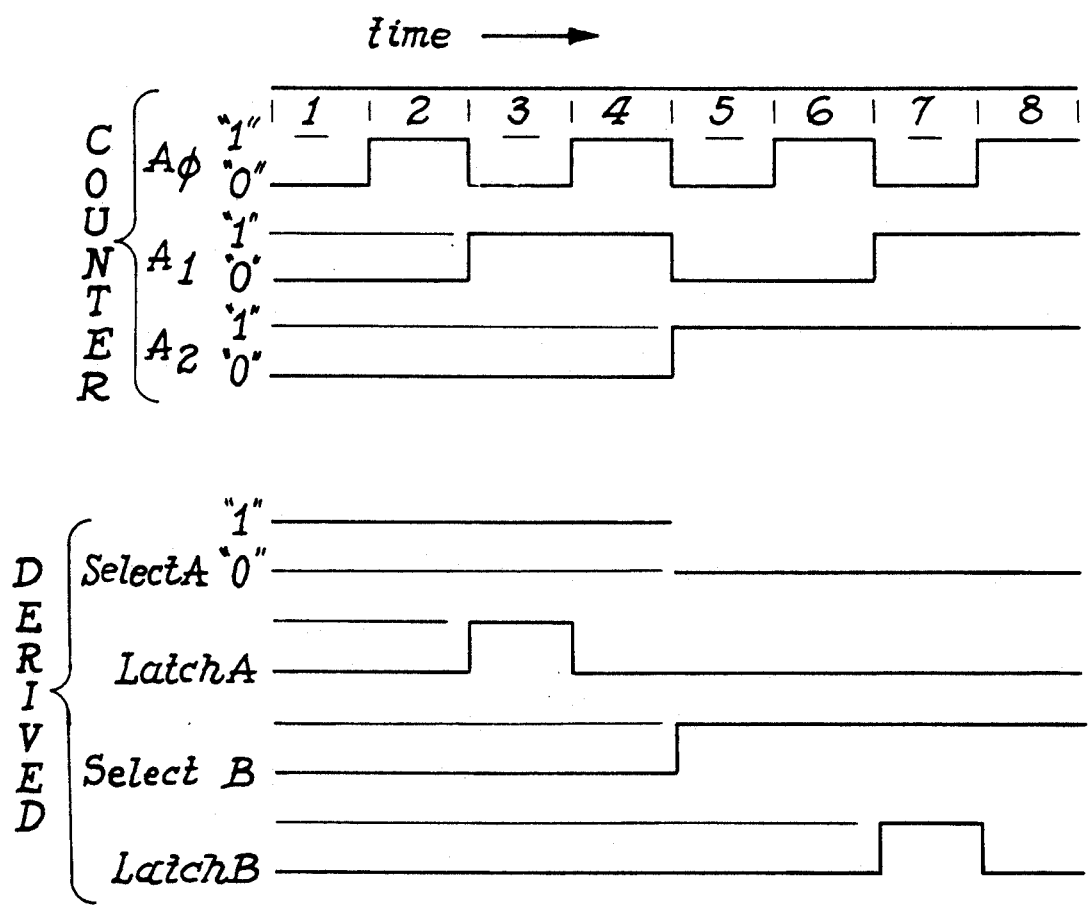
FIG. 3 is a timing diagram showing typical clock intervals and control signals.

The sequencing circuit C controls the alternate operation of the probe 10 to read the dynamic dielectric constant or the electrical conductivity, as well as the latching of the digital data in circuits A and B. In sequencing circuit C as illustrated in FIG. 2, the clock 20, comprising for example, a free-running oscillator, provides a clock input of pulses to the binary counter 21. In the embodiment, the last three stages of the counter 21 are decoded to provide respective select signals to the switch 12 and latch signals to the latches 16 and 19. Three address lines 31, 32, 33 are connected to the three decoded stages of counter 21 to provide sequentially and repetitively 8 clock pulses in the sequencing circuitry. The clock pulses are sequenced through a gating system 34 and selectively transmitted in accordance with the logic of the gating system 34 and the clock pulses. FIG. 3 is a chart diagramming the pulsing through the address lines 31, 32 and 33 and the decoding of the signals carried outin the gating system 34 and illustrating the operation of the gating system 34. The eight clock intervals are illustrated horizontally on the chart and the address lines 31, 32 and 33 and the select and latch signals are illustrated vertically.

During intervals 1 through 4, the A circuit is selected, and the B circuit is disconnected. During interval 3, the latch input is gated to its output. At the end of the interval 3, the comparator A output is latched, and will not change until interval 3 of the next set of 8 clock intervals. During intervals 5 through 8, circuit B is selected and circuit A is disconnected. During interval 7, the comparator B output is latched.

The display logic decoded from the outputs of comparators 15 and 18 as stored in latches 6 and 19 has been described above.

The present invention as illustrated in the abovedescribed embodiment employs dynamic dielectric constant and electrical conductivity to detect a phase change from water to ice. The difference between the dynamic dielectric constant of water and ice is illustrated by the example given in the graph of FIG. 4. In this example, a probe shown in FIG. 5 measured the dynamic dielectric constant and electrical conductivity of distilled water, rain water, water with impurities dissolved or suspended, and ice. The probe 10 was cooled from 20° C. to −4° C. on a cold plate 35. The system and its operation are insensitive to dirt or chemical impurities which may be present.

As shown in FIG. 4, the difference between the dynamic dielectric constant of water and ice at frequencies near 1 MHz is about two orders of magnitude. Dyanmic dielectric constant shown on the abscissa and frequency on the ordinate.

In a modification of the system the recording means receives the signals of the presence or absence of ice on a surface by simultaneous measurements of electrical conductivity and dynamic dielectric constant with separate conductivity and dielectric electrodes and simultaneously producing output voltages from the simultaneous measuring of conductivity and dynamic dielectric constant. As described above, voltage-to-digital converters produce coded signals representing the output voltages stored and then extracting the stored signals and decoding the extracted signals to produce a combination of pulses from said output voltages. The recording means receiving the pulses signaling the condition of the surface.

According to this invention, the capacitancetype probe is adaptable to a wide variety of designs and configurations as the effectiveness of the system in monitoring icing conditions is independent of probe geometry. The following examples of effective probe designs are described to illustrate this invention and are not intended as limitative.

Figure 6:
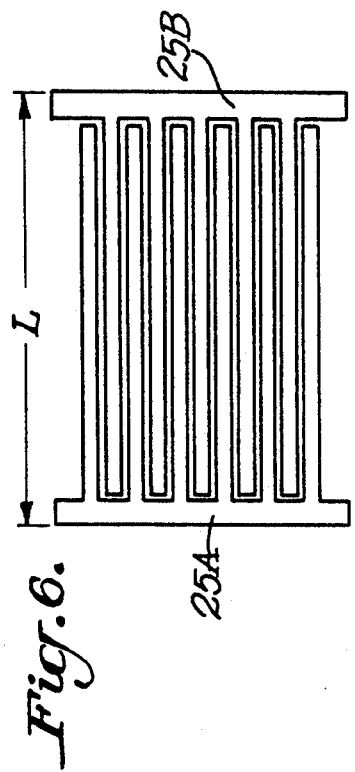
FIG. 6 is a plane view of a metal foil etched probe according to this invention.
Figure 5:
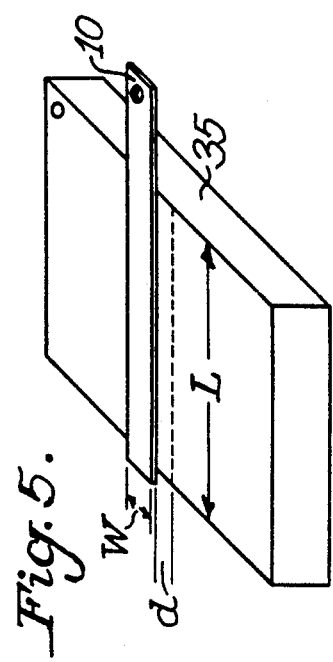
FIG. 5 is a perspective view of a capacitor probe of simple geometry according to this invention.

Four types of probes were designed and tested. Probe 1 was the capacitance-type probe as shown in FIG. 5 illustrating the laboratory model. A prototype was also made of vacuum deposited aluminum on a plastic backing. The electrodes were engraved mechanically and the probe was attached to a fiberglass insulation. A copper foil etched probe is illustrated in FIG. 6.

The electrode geometric parameters d, l, and w are determined from the scaling graph in FIG. 7.

Testing the large and small copper foil probes showed that the measured value of the dielectric constant of water was constant, independent on the probe geometry and electronics.

Testing of this type of metal foil probe showed that both aluminum and copper were acceptable metals for the probe construction. The insulating material, fiberglass, also performed well. Testing did show that there is a threshold thickness of insulation below which the signal is distorted.

The sensing probe may have a part of the monitored surface as one electrode. The electrode may be made of metal resistant to biological fouling and corrosion, such as copper alloy or silver and its alloys. Electrodes comprised of an erosion resistant alloy such as stellite are also effective in the present invention and are suitable for such applications as on road surfaces.

An illustration of test results with an electronic circuit in keeping with the apparatus described above and illustrated in FIGS. 1 and 2 is shown in the chart of FIG. 8.

In the chart of FIG. 8, the ordinate represents the output voltage of the icing measurement circuit, the abscissa represents time as recorded. The voltage changes from detection of conditions by the above described apparatus are illustrated by the solid black line in an optimization of representative test results. It is zero volts for water and air and 15 volts for ice. Several probes were used in the laboratory and field testing and the electronic equipment functions with all of them.

The legends indicate the varying conditions detected over the time period represented by the abscissa. The voltage jumps to 15V with the formation of ice and decreases to 0V when the prevailing conditions are rain water, air, water containing impurities, and diluted deicer liquid. Viewing the abscissa as a recording sheet it will be seen that the apparatus provides a record of changing conditions, such as ice accumulation.

The above described embodiment exemplifies the present invention. However, this invention is not limited to the arrangement of electrodes specifically described above and illustrated in the figures. It will be apparent that other embodiments can be provided without departing from the spirit of the invention.

For example, the electrodes and accompanying circuitry can be positioned in a refrigerated enclosure, such as a refrigerator, at a place where unwanted ice forms during operation. The electrodes through the circuitry of this invention will signal the formation of ice and produce pulses which actuate defrosting means on detecting a formation of a predetermined amount of ice.

This embodiment is advantageous in providing a system for actuating refrigerator defrosting apparatus only when it is needed. A similar use could be arranged in determining frost formation for the actuation of a frost prevention apparatus.

Another modification employing this invention is positioning spaced apart a plurality of electrodes each with a detecting means of a dynamic dielectric contact measuring circuitry and conductivity measuring circuitry.

The spaced apart electrodes define an area. In this area the electrodes by detecting ice can detect and signal the growth of ice as the formation of ice is separately detected and reported by the individual spaced apart electrodes. Stated otherwise, quantitative measurement voltages across a series of electrodes detect the rate of ice accumulation by the progressive signaling in the successive system or ice thickness. When an array of electrodes is positioned vertically in a body of water, such as a river or ocean, thickness of the ice cover can be automatically measured.

Another embodiment of the invention involving some modification occurs in the arrangement of a signaling and recording system in an apparatus for measuring the speed of ice formation. In this embodiment a suitable heating means is associated with the electrodes so as to be able to melt ice that forms at the surface at the electrodes. By periodically melting ice at the surface with a heater and then detecting the subsequent ice formation and recording that ice formation in a timed relation it becomes possible to easily detect the rate of ice accumulation. One important utilization of this modified embodiment is in the detection of the rate of formation of ice in freezing rain.

As pointed out above, this advance is relatively unaffected by conditions of operation such as distilled and rain water, wet and dry snow, freezing rain, humid air, tap water, and water and ice contaminated with road salt, acids, defrosting chemicals, and dirt.

Voltage as used herein refers to electrical potential, or potential expressed in volts. Potential refers to a degree of electrification.

What is claimed:

1. A method of determining and reporting the formation of ice on a capacitor probe, in an environment being monitored,
    comprising the steps of using capacitor electrodes at a surface and circuits for applying potentials at said electrodes including an electrode of said capacitor electrodes which is switchedly connected to a circuit for measuring electrical conductivity at the electrodes and connected to a circuit for measuring dynamic dielectric constant of air, water or frozen water at a frequency near 1 MHz at the electrodes,
    measuring the electrical conductivity of a substance which is air, water or frozen water at the electrodes to produce a d.c. potential level and latching the potential level in a first latch means,
    measuring the dynamic dielectric constant of a substance which is air, water or frozen water at the electrodes to produce a d.c. potential level and latching the potential level in a second latch means using said latched potentials to form signal pulses.
    and actuating recording means with said signal pulses to signify conditions of dry, wet, and ice at the surface.

2. The system as claimed in claim 1 wherein one electrode of said capacitor electrodes is a part of the surface.

3. A method as claimed in claims 1 or 2 wherein the capacitor electrodes are suspended in the monitored environment.

4. A method as claimed in claims 1 or 2 wherein multiple pairs of electrodes move in and out of the monitored environment thus allowing monitoring of ice or water accretion vs. time.

5. A method as claimed in claims 1 or 2 wherein the ice and water are cleared from the unexposed capacitor electrodes.

6. A method as claimed in claim 3 wherein multiple pairs of electrodes move in and out of the monitored environment thus allowing monitoring of ice or water accretion vs. time.

7. A method as claimed in claim 3 wherein the ice and water are cleared from the unexposed capacitor electrodes.

8. A method as claimed in claim 4 wherein the ice and water are cleared from the unexposed capacitor electrodes.

* * * * *